United States Patent [19]

Commandeur et al.

[11] Patent Number: 5,173,477
[45] Date of Patent: Dec. 22, 1992

[54] POLYPHENYLMETHANE HEAT-SENSITIVE RECORDING MEDIA

[75] Inventors: Raymond Commandeur, Vizille; Jean-Pierre Sarron, Chatou, both of France

[73] Assignee: Société Atochem, Puteaux, France

[21] Appl. No.: 810,181

[22] Filed: Dec. 19, 1991

[30] Foreign Application Priority Data

Dec. 19, 1990 [FR] France .................. 90 15922

[51] Int. Cl.$^5$ .......................... B41M 5/30
[52] U.S. Cl. ..................... 503/208; 503/209; 503/225
[58] Field of Search ............ 503/208, 209, 225

[56] References Cited

FOREIGN PATENT DOCUMENTS 0367228 5/1990 European Pat. Off. ............ 503/209

Primary Examiner—Pamela R. Schwartz
Attorney, Agent, or Firm—Burns, Doane, Swecker & Mathis

[57] ABSTRACT

Novel heat-sensitive recording media include a support substrate, e.g., paper or a synthetic polymer film, having a thermosensitive recording layer deposited thereon, such thermosensitive recording layer comprising a colorant precursor, a heat-sensitive developer therefor and at least one polyphenylmethane of the formula (A1):

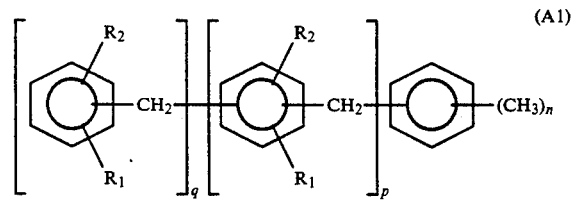

in which $R_1$ and $R_2$, which may be identical or different, are each a halogen atom, $NO_2$, $CN$, $OCH_3$, $H$ or an alkyl radical having up to 5 carbon atoms; n is 3, 4 or 5; p is 1, 2 or 3; g is 0 or 1 and the maximum value of p+g is 2; and the melting point of which polyphenylmethane being at least 50° C.

4 Claims, 2 Drawing Sheets

POLYPHENYLMETHANE HEAT-SENSITIVE RECORDING MEDIA

BACKGROUND OF THE INVENTION

1. Field of the Invention

The present invention relates to certain heat-sensitive recording materials comprised of particular polyphenylmethanes and to thermal papers useful in computer printers or facsimile machines comprised thereof.

This invention especially relates to such heat-sensitive recording materials comprising, e.g., a paper substrate, onto which a colorant precursor and a developer are deposited which, under the influence of heat, coloration is produced from said precursor and developer.

2. Description of the Prior Art

EP-164,417 describes improved heat-sensitive recording materials produced by incorporating with such precursor and developer an optionally substituted benzylbiphenyl or terphenyl which may also be hydrogenated.

Consistent therewith, improved quality is attained, together with a higher printing velocity.

U.S. Pat. No. 4,742,042 describes materials similar to the above, but in which the benzylbiphenyl may be replaced by esters or diesters.

The biphenyls and the terphenyls are expensive to prepare as they require high temperature processes.

According to Ullman's, *Encyclopedia of Industrial Chemistry*, 5th edition, Vol. A 13, pages 261-265, biphenyl is produced by the hydrodealkylation of toluene at 700° C. and the terphenyls by the dehydrocondensation of benzene at a temperature ranging from 700° to 850° C.

SUMMARY OF THE INVENTION

A major object of the present invention is the provision of novel polyphenylmethane heat-sensitive recording media.

Briefly, the present invention features novel heat-sensitive recording media comprising a substrate layer containing a colorant precursor and a heat-sensitive developer, such substrate layer also including a polyphenylmethane of formula (A1):

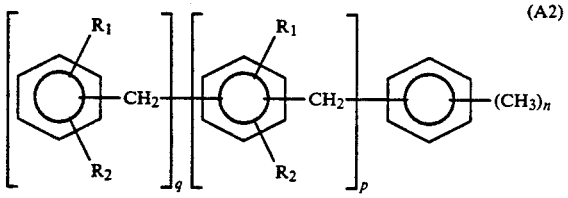

wherein $R_1$ and $R_2$, which may be identical or different, are each a halogen atom, $NO_2$, $CN$, $OCH_3$, H or alkyl radical having up to 5 carbon atoms; n is 3, 4 or 5; p is 1 or 2; q is 0 or 1 and p+q is a maximum of 2; and wherein the melting point thereof is higher than 50° C.

DETAILED DESCRIPTION OF THE PREFERRED EMBODIMENTS OF THE INVENTION

Figure 1:
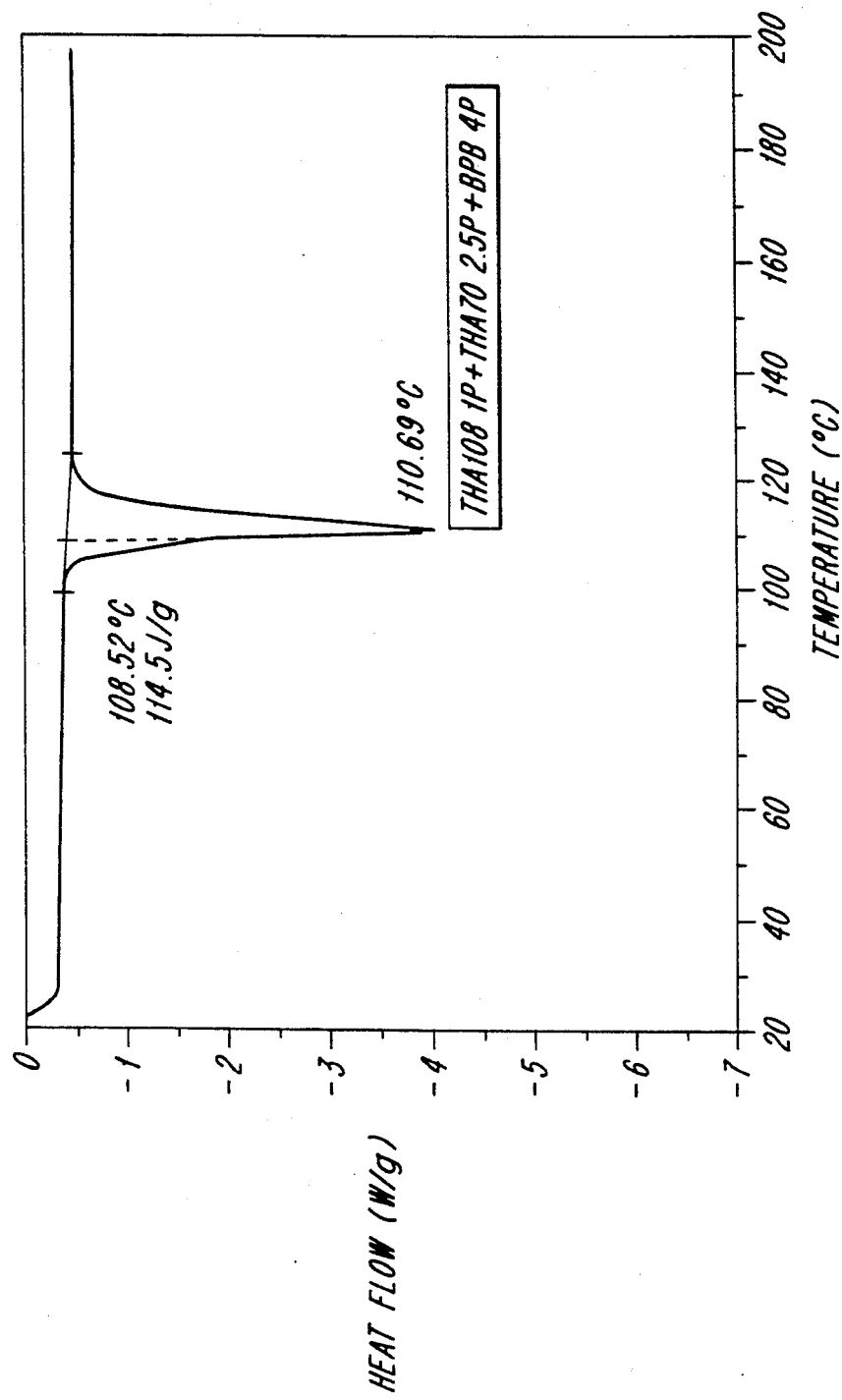
FIGS. 1 and 2 are thermograms of compositions of materials for recording layers according to the instant invention.

More particularly according to the present invention, while all of the (A1) compounds are suitable if the heat-resistant recording material comprises a substrate such as paper or a synthetic resin film, such compounds having a melting point ranging from 50° to 220° C. are advantageously used. Particularly preferred are those compounds wherein $R_1$ and $R_2$ are $CH_3$, Cl and H.

These compounds may be prepared by a Friedel and Crafts condensation of:

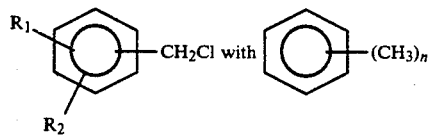

This basic reaction is well known to this art. The catalyst therefor is a halide or an inorganic acid, for example ferric chloride, antimony trichloride, titanium tetrachloride or aluminum chloride. It is also possible to use sulfuric acid or the zeolites. It suffices to contact the two reagents with the catalyst. Upon completion of the reaction, a distillation may be carried out to eliminate any excess of either one of the reagents.

It is also possible to eliminate, following the distillation of the excess of the reagent or reagents, the Friedel and Crafts catalyst by any known means, such as washing with water, neutralization, drying.

In the particular case of the compounds wherein $R_1$ and $R_2$ are $CH_3$ and n is 3, it is possible to prepare the $(CH_3)_2C_6H_3CH_2Cl$ chloride in situ, i.e., the process commences with $(CH_3)_3C_6H_3$, which is partially chlorinated by radical chlorination, whereupon a Friedel/Crafts catalyst is added to the reaction medium, comprising a mixture of $(CH_3)_2C_6H_3CH_2Cl$ and $(CH_3)C_6H_3$. Friedel/Crafts condensation is then carried out as described above. The radical chlorination of aromatic hydrocarbons is also known to this art. Such a method, for toluene, is described in EP-136,230. It suffices upon completion of the reaction to recover the products by distillation.

Certain of the compounds of Formula (A1) are novel. The present invention thus also features the compounds of formula (A2):

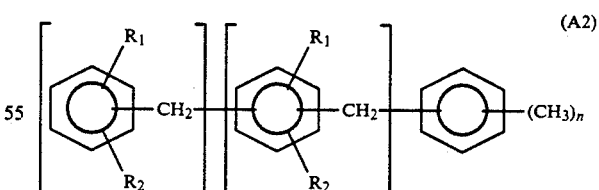

wherein $R_1$ and $R_2$, which may be identical or different, are each selected from among a halogen atom, $NO_2$, $CN$, $-OCH_3$, H or an alkyl radical having up to 5 carbon atoms; n is 3, 4 or 5; p is 1, 2 or 3; q is 0 or 1 and p+q is a maximum of 2; and the melting point thereof being higher than 50° C., and the compounds wherein:
(a)
q=0,
p=1, $R_1=CH_3$—in ortho position, $R_2=$a halogen or H, (b)

$q=0$,
$p=1$,
$R_1=CH_3$—in ortho position, $R_1=$a halogen or H being excluded.

Advantageously, compounds wherein $q=0$, $p=1$ and $R_1$ and $R_2$ are selected from among H and $CH_3$, are used.

The manufacture of such recording materials/media is per se known to this art.

In order to further illustrate the present invention and the advantages thereof, the following specific examples are given, it being understood that same are intended only as illustrative and in nowise limitative.

EXAMPLE 1

Into a reactor equipped with a rotary agitator, a thermometric casing and a chlorine injector, the following materials were introduced:

(i) 3.33 moles of mesitylene (400 g) containing 150 mg of azobisisonbutyronitrile (AIBN).

The mixture was heated to 150° C. and 1 mole chlorine was introduced over one hour with the simultaneous introduction of 350 mg AIBN in solution in 0.67 mole of mesitylene (80 g).

The reaction medium was then degassed with nitrogen and placed into a pouring funnel. It was introduced into a reactor equipped with a rotary agitator, into which 1.9 mole of mesitylene (228 g) and 2.2 g ferric chloride anhydride were charged. The temperature was 140° C. and the duration of the pouring is 1 hour. The reaction was continued for another 2 hours, 30 min, at 150° C. after the additional introduction of ferric chloride. The reaction medium was subjected to, after degassing, to distillation with a column of approximately 4 plates under a vacuum of 10 mm mercury to eliminate the unreacted mesitylene. The vacuum was then decreased to 1 mm mercury. 90 g of a fraction distilling at 151° C. and including the following compound were obtained:

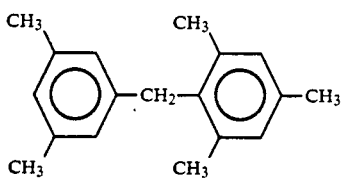

the melting point of which was 66° C. and the purity according to chromatographic analysis was 97.8%. It was a white solid, colorless in the molten state. The residual chlorine content was 500 ppm.

EXAMPLE 2

Into a reactor equipped with a rotary agitator, a reflux condenser, a thermometric casing, a nitrogen injector, 4 moles of durene (537) heated to 140° C., Were introduced. 2.1 g ferric chloride were added and, by means of a pouring funnel, 1.33 mole of benzoyl chloride (168 g) were introduced over 1 hour under a flow-stream of nitrogen. 0.5 g $FeCl_3$ was added and the reaction continued for 3 hours at 140° to 150° C. The hydrochloric acid evolved was collected in a water bubbler and represented 96% of theoretical.

The reaction medium was then subjected directly to distillation using a column having approximately 4 plates in a vacuum of about 15 mm mercury. Following the separation of the unreacted durene, the distillation column was removed and distillation continued. A fraction distilling at 184° to 185° C. in a vacuum of 15 mm mercury was obtained; it included a benzyldurene:

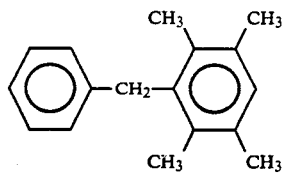

the weight of 200 g of which represented a yield of 67% relative to the benzyl chloride used. The purity determined by chromatographic analysis was 98.2%. The melting point was 55° C. It was a white solid, colorless in the molten state. The product has a chlorine content of less than 20 ppm.

EXAMPLE 3

The condensation of benzyl chloride with pentamethylbenzene was carried out according to the procedure of Example 2, but using a molar benzyl chloride/pentamethylbenzene ratio of 1/5.

Following the reaction and distillation, a fraction distilling at 202° to 206° C. (under 10 mm of mercury) of benzylpentamethylbenzene was obtained:

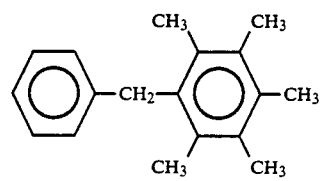

in a yield of 73% relative to the benzyl chloride introduced.

The chromatographic purity was 98.8% and the melting point was 112° C. The material was a white solid, colorless in the molten state. The chlorine content thereof was less than 20 ppm.

EXAMPLE 4

The condensation of orthomethylbenzyl on durene was carried out according to the procedure of Example 2, but employing a molar ratio of orthomethylbenzyl/durene=1/5.

After the reaction and distillation, a fraction distilling at 213° to 217° C. under 32 mm mercury of the compound of the following formula was obtained:

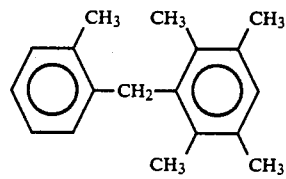

in a yield of 53% relative to the orthomethylbenzyl introduced.

The chromatographic purity was 98.1% and its melting point was 98° C. It was a white solid, colorless in the molten state.

EXAMPLE 5

The procedure of Example 4 was repeated, but replacing the orthomethylbenzyl chloride with paramethylbenzyl chloride. After the reaction and distillation, a fraction distilling at 213° to 214° C. under 25 mm mercury, of the following formula, was obtained:

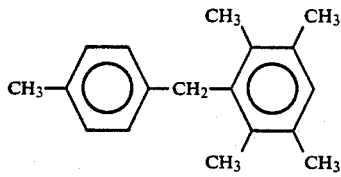

in a yield of 68% relative to the paramethylbenzyl chloride introduced.

The chromatographic purity was 97.1% and the melting point was 105° C.

EXAMPLE 6

The procedure of Example 2 was repeated, but using parachlorobenzyl chloride in the molar ratio of parachlorobenzyl chloride/durene of ⅓.

After the reaction and distillation, a fraction distilling around 214° to 217° C. under a vacuum of 16 mm mercury of parachlorobenzyldurene was obtained:

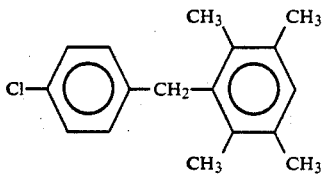

in a yield of 70% relative to paraxylyl chloride introduced.

The chromatographic purity was 99.3% and its melting point was 102° C. It was a white solid, colorless in the molten state.

Distillation was carried out on the distillation residue under a vacuum of 6 mm mercury.

Distillation was continued on the distillation residue under a vacuum of 6 mm mercury. A fraction distilling at 270° to 280° C. including bis(parachlorobenzyl)durene was obtained.

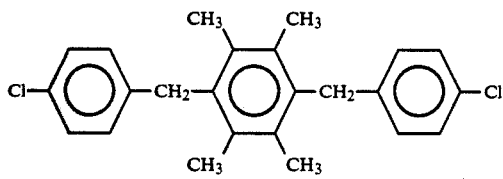

The chromatographic purity was 91.8% (still containing 3.6% parachlorobenzyldurene) and its melting point was 210° C.

EXAMPLE 7

The procedure of Example 2 was repeated, but entailing the condensation of benzyl chloride with mesitylene, in a molar ratio of benzyl chloride/mesitylene equal to ½.

After the reaction and distillation, a fraction distilling at 164° to 165° C. under a vacuum of 12 mm mercury, of benzylmesitylene was obtained:

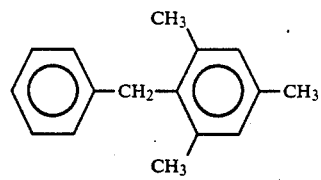

in a yield of 59%. The chromatographic purity was 98.5%. It was a liquid at ambient temperature.

The distillation was continued on the residue under a vacuum of 12 mm mercury and a fraction distilling at 245° to 246° C. and including dibenzylmesitylene was obtained:

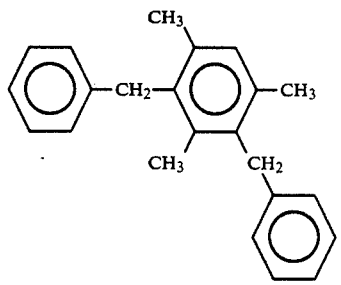

The chromatographic purity was 93.5% and its melting point was 73° C.

EXAMPLE 8

The intimate grinding of 4 parts of benzylpentamethylbenzene (BPB) obtained in Example 3, with one part of THA 108 (commercially available "color former") and 2.5 parts of THA 50 (commercially available "color developer") provided a single peak via thermal analysis; as indicated in FIG. 1, the compound was useful as a sensitizer for the manufacture of thermal paper.

EXAMPLE 9

Figure 2:
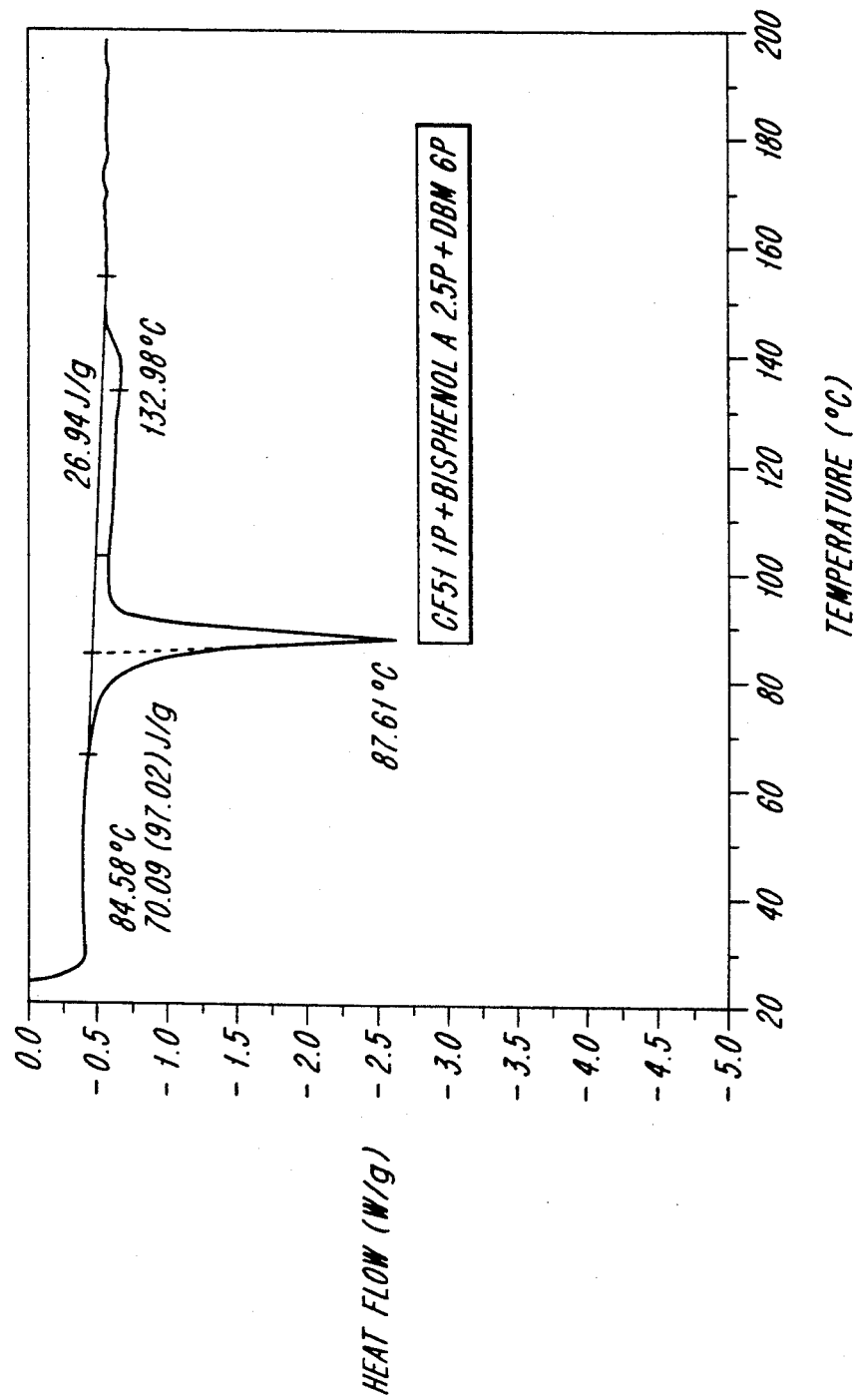

The intimate grinding of 6 parts of dibenzylmesitylene (DBM) prepared by the procedure of Example 7 (purity 96% F=89%) with one part of CF 51 (commercially available "color former") and 2.5 parts bisphenol A provided a mixture, the thermogram of which (FIG. 2) confirmed that the compound was useful as a sensitizer for the production of thermal paper.

DBM combined with a "color former" and a "color developer", then coated onto paper by methods similar to those described in EP-164,417 or EP-343,014, produced a heat-sensitive paper useful for telecopying applications.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A heat-sensitive recording material including a support substrate having a thermosensitive recording layer deposited thereon, said thermosensitive recording layer comprising a colorant precursor, a heat-sensitive developer therefor and at least one polyphenylmethane of the formula (A1):

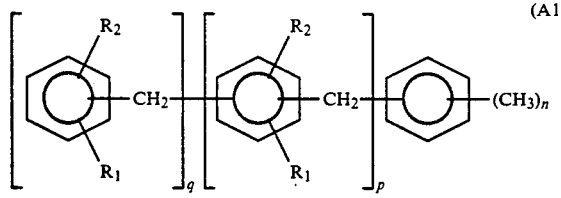

in which $R_1$ and $R_2$, which may be identical or different, are each a halogen atom, $NO_2$, CN, $OCH_3$, H or an alkyl radical having up to 5 carbon atoms; n is 3, 4 or 5; p is 1 or 2; q is 0 or 1 and the maximum value of p+q is 2; and the melting point of which polyphenylmethane being at least 50° C.

2. The heat-sensitive recording material as defined by claim 1, the melting point of said polyphenylmethane (A1) ranging from 50° to 220° C.

3. The heat-sensitive recording material as defined by claim 1, wherein $R_1$ and $R_2$ are each $CH_3$, Cl or H.

4. The heat-sensitive recording material as defined by claim 1, wherein said support substrate comprises paper or a synthetic polymer film.

* * * * *

UNITED STATES PATENT AND TRADEMARK OFFICE
CERTIFICATE OF CORRECTION

PATENT NO. : 5,173,477
DATED : December 22, 1992
INVENTOR(S) : Raymond COMMANDEUR et al.

It is certified that error appears in the above-indentified patent and that said Letters Patent is hereby corrected as shown below:

In column 3, line 60, delete "benzoyl" and insert --benzyl-- therefor;

In column 4, line 49, after "orthomethylbenzyl" insert --chloride--.

Signed and Sealed this

Fifteenth Day of March, 1994

Attest:

BRUCE LEHMAN

Attesting Officer

Commissioner of Patents and Trademarks